(12) United States Patent
Analoui (10) Patent No.: US 6,405,071 B1
(45) Date of Patent: Jun. 11, 2002

(54) THREE DIMENSIONAL IMAGING AND ANALYSIS OF A ROOT CANAL

(75) Inventor: Mostafa Analoui, Carmel, IN (US)

(73) Assignee: Advanced Research and Technology, Indianapolis, IN (US)

( * ) Notice: Subject to any disclaimer, the term of this patent is extended or adjusted under 35 U.S.C. 154(b) by 0 days.

(21) Appl. No.: 09/501,749

(22) Filed: Feb. 10, 2000

(51) Int. Cl.⁷ .................................................. A61B 6/00
(52) U.S. Cl. ...................... 600/425; 128/922; 382/132; 433/215; 345/419
(58) Field of Search ............................... 600/425, 407; 128/920, 922; 345/419; 433/215; 382/128, 132

(56) References Cited

U.S. PATENT DOCUMENTS

| | | |
|---|---|---|
| 4,447,206 A | 5/1984 | Ushiyama |
| 4,850,866 A | 7/1989 | Gutierrez et al. |
| 5,017,134 A | 5/1991 | Saito et al. |
| 5,211,556 A | 5/1993 | Kobayashi et al. |
| 5,295,833 A | 3/1994 | Chihiro et al. |
| 5,562,448 A | 10/1996 | Mushabac |
| 5,706,814 A | 1/1998 | Nonomura |
| 5,842,858 A | 12/1998 | Truppe |
| 5,880,962 A | 3/1999 | Anderson et al. |
| 5,897,315 A | 4/1999 | Nakayama et al. |

*Primary Examiner*—Ruth S. Smith
(74) *Attorney, Agent, or Firm*—Maginot, Moore & Bowman (57) ABSTRACT

A computer-based imaging technique for three dimensional modeling of root canal shape and accurate measuring of root canal length is provided. A direct digital radiology (DDR) system that replaces film by an electronic sensor is used to acquire radiographic images of the root canal. The DDR system allows instant radiographic imaging with significantly less patient exposure than conventional film-based radiography. Additionally, since the images are captured in digital form, a computer is used for processing. In accordance with one aspect of the present invention, two digital images of the dentition from two different angles are acquired. The root canal in each image, along with the direction of projection will define a surface in 3-D space. The intersection of two surfaces will represent the root canal in 3-D. Once the 3-D shape of the root canal is reconstructed, the length of the root canal can be obtained by computing the length of the 3-D curve. The measured length will be scaled appropriately to include the pixel size and magnification due to projection. A computer program will carry out the process of detection of the root canal in each image, surface computation, length measurement, and calibration, with minimal user interaction. The computed model is rendered on a computer screen along with interactive options for viewing, rendering and superimposition on the radiographic image.

19 Claims, 5 Drawing Sheets

THREE DIMENSIONAL IMAGING AND ANALYSIS OF A ROOT CANAL

BACKGROUND OF THE INVENTION

1. Field of the Invention

The present invention relates to a method and apparatus for a dental procedure, and, more particularly, to a method and apparatus for determining the dimensions of a root canal of a tooth.

2. Description of the Related Art

Figure 1:
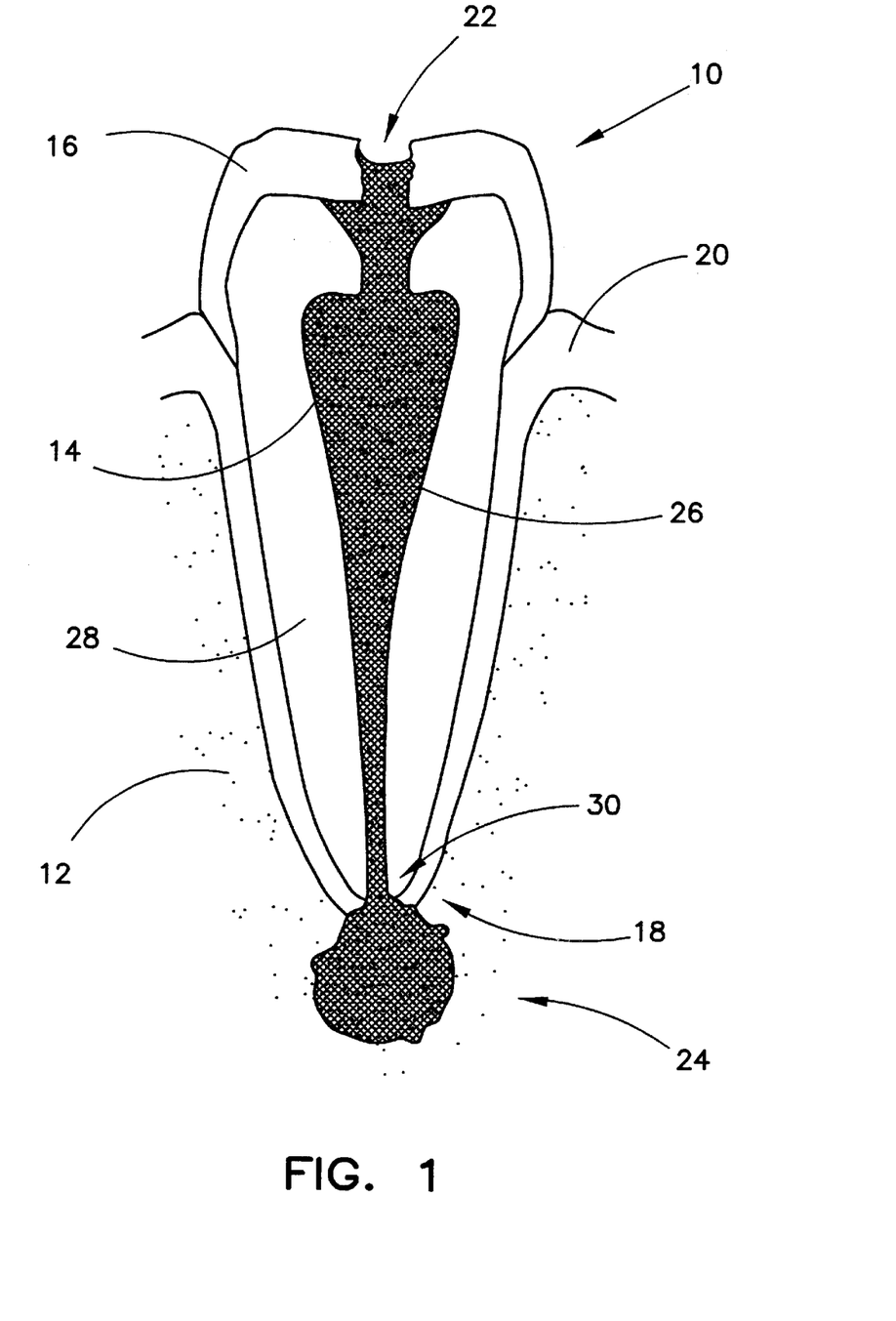
FIG. 1 is a side sectional view of an infected tooth in the jawbone of a patient.

As is known, and referring to FIG. 1, pulp 14, the soft tissue that contains nerves, blood vessels and connective tissue, lies within a tooth 10 in the gum 20 and extends down from the crown 16 of the tooth thereof to the tip 18 of the root in the bone 12 of the jaw. When the pulp 14 is diseased or injured, and cannot repair itself, it dies. The most common cause of pulp death is a cracked tooth or a deep cavity 22, typically caused by decay. Both of these problems can result in germs/bacteria entering the pulp 14. Germs can cause an infection inside the tooth 10. Left without treatment, pus 24 builds up at the root tip 18 and can cause damage to the bone 12 around the infected tooth 10. When the infected pulp is not removed, pain and swelling can result. Certain byproducts of the infection can injure the jawbone. Without treatment, the infected tooth 10 may have to be removed.

One common method of treating the above-described infection before it reaches the bone 12 is to perform a dental procedure commonly referred to as a "root canal" treatment. This procedure involves removal of infected nerve and vascular tissue from a patient's root canal 26 of the tooth 10 before such infected matter has a chance to further infect the patient's bone 12 which is located adjacent to the root canal 26. This infected matter is removed from the root canal 26 utilizing a drill fitted with an endodontic file. In particular, the endodontic file is manipulated to advance through the crown 16 of the infected tooth 10 until the endodontic file extends into the root canal 26. Thereafter, the endodontic file is manipulated within the root canal 26 until all of the infected nerve and vascular tissue are removed from the root canal 26. Once the nerve and vascular tissue are removed, the root canal 26 is sterilized and filled with an inert material and cement.

A problem with the above-described root canal procedure is that a clinician performing the procedure must ensure that the endodontic file reaches all of the infected areas of the root canal 26 without the endodontic file being erroneously advanced through a distal wall 30 (i.e. apical foramen) of the root canal 26. Therefore, in order to perform a root canal procedure correctly, it is important that the clinician know the length of the root canal 26 so that he/she does not over advance the endodontic file into the root canal 26 and thus drill a hole through the distal wall 30 (i.e. apical foramen) of the infected tooth 10 which may result in the infection being propagated to the bone 12.

Root canal therapy thus encompasses may clinical steps, each one predicated upon an accurate and precise determination of the length of the root canal of the tooth. From an accurate root canal measurement the clinician can determine the drilling distance and the point to which root canal fill material should be placed. This is termed the "working length". The working length is defined as the distance from a coronal (i.e. crown) reference point on the tooth to the point at which canal preparation and obturation should be terminated. Failure to determine an optimal root canal working length can lead to instrumentation short of the desired length with the result of tissue remnants being left in the root canal. Such failure to determine optimal root canal working length could also lead to long instrumentation with concomitant damage to the periradicular tissues, increased patient discomfort, potential for development of infection or inflammation, and the placement of irritating material beyond the confines of the tooth.

Heretofore, clinicians attempted to resolve the problem of determining root canal length by obtaining a conventional X-ray of the infected tooth and then estimating the length of the root canal by measuring the image of the root canal formed on the X-ray film. However, this approach suffers from the fact that most root canals are curved in such a way that an X-ray image is only two dimensional (i.e. the root canal is shown extending in the X and Y directions only), and it is common for the root canal to extend in a third dimension (i.e. the Z direction). Therefore, based on the data provided to the clinician by the X-ray image, it is still difficult for the clinician to determine the length of the root canal. This results in the likelihood that a clinician during a root canal procedure would either (i) over advance the endodontic file through the distal wall of the root canal of the infected tooth thereby creating a possibility that the bone will become infected, or (ii) under advance the endodontic file relative to the distal wall of the root canal thereby resulting in an amount of the infected nerve and vascular tissue not being removed from the root canal during the root canal procedure.

Thus, the generally accepted methods for determining the working length of a root canal are based on the placement of an endodontic file in the root canal and/or periapical radiographs. In using endodontic files, inaccurate placement of the stop and its angle can cause measurement error of 1 mm or more. Moreover, dental radiographs depict a two-dimensional (2-D) projection of the root canal, which can lead to errors in measurement for canals with significant curvature. An accurate measurement of length of the root canal requires a complete three-dimensional (3-D) description of the root canal.

What is needed is a technique and apparatus for an accurate 3-D measurement of the dimensions of a root canal.

SUMMARY OF THE INVENTION

The present invention provides a system and method for imaging and determining the dimensions of a root canal of a tooth. In particular, the present system and method generates a three dimensional mathematical model of a root canal by analyzing X-ray images. Thereafter, the dimensions of the root canal may be calculated based on the three dimensional mathematical model. This results in highly accurate imaging and measurement of the dimensions (i.e. length) of the root canal regardless of the anatomical shape of the root canal.

In one form thereof, the system includes a digital image (e.g. radiographic) sensor or transducer, a source of radiation such as an X-ray generator, and a computer or processing circuitry for receiving and storing digital X-ray images (radiographs) captured by the sensor and operating on the digitized images, and a display. The sensor is preferably an electronic type X-ray sensor.

In one form thereof, the method includes obtaining a first radiograph of the root canal by the digital image sensor upon exposure by generated X-rays which is digitized and stored by the computer. The first radiograph is representative of the root canal being interposed between the X-ray source and the image sensor at a first orientation. Thereafter, the source of radiation and image sensor is repositioned relative to the root canal so that the root canal is interposed between the source of radiation and the image sensor at a second orientation. Such repositioning may, for example, be between 5–40° relative to the first position. The angular change in positioning can be either set by the operator or detected based on a three dimensional reference object embedded in the bite-olock. A second radiograph of the root canal is captured by the image sensor which is as well digitized and stored by the computer. The first and second digitized radiographs are processed by the computer to obtain a three dimensional mathematical model of the root canal. Thereafter, an image of the root canal may be shown on the display and/or the dimensions (e.g. length) of the root canal may be calculated by the computer. Such display and/or dimensions are then utilized by the clinician to carry out a root canal procedure.

In accordance with an aspect of the present method, after image acquisition, the computer processes the two radiographs and determines the edges of the root canal. The edges to each image are determined by one or all of: 1) either filtering for noise or searching and replacing dead and overexposed pixels with the mean gray level of neighboring pixels; 2) computing a single threshold of the entire radiograph for segmenting the radiograph; 3) using a morphological skeleton computation to obtain a central line of the root canal; and 4) modeling the root canal by an $n^{th}$ order polynomial. Once the edges for each image are detected and modeled, the 3-dimensional surfaces are computed by the use of a projection matrix for each image. The intersection of the 3-dimensional surfaces defines the 3-dimensional model of the root canal.

In accordance with an aspect of the present invention, once the 3-dimensional model of the root canal has been determined, it can either be displayed on the display or its dimensions (e.g. length and curvature) may be calculated.

An advantage of the present invention is the improved quality of root canal treatment by increasing the accuracy of working length measurement.

Another advantage of the present invention is the increased chance of detecting horizontal and vertical root fracture.

Yet another advantage of the present invention is the reduction of treatment time and cost.

Still further an advantage of the present invention is increased patient comfort and the reduction of radiation exposure.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 2:
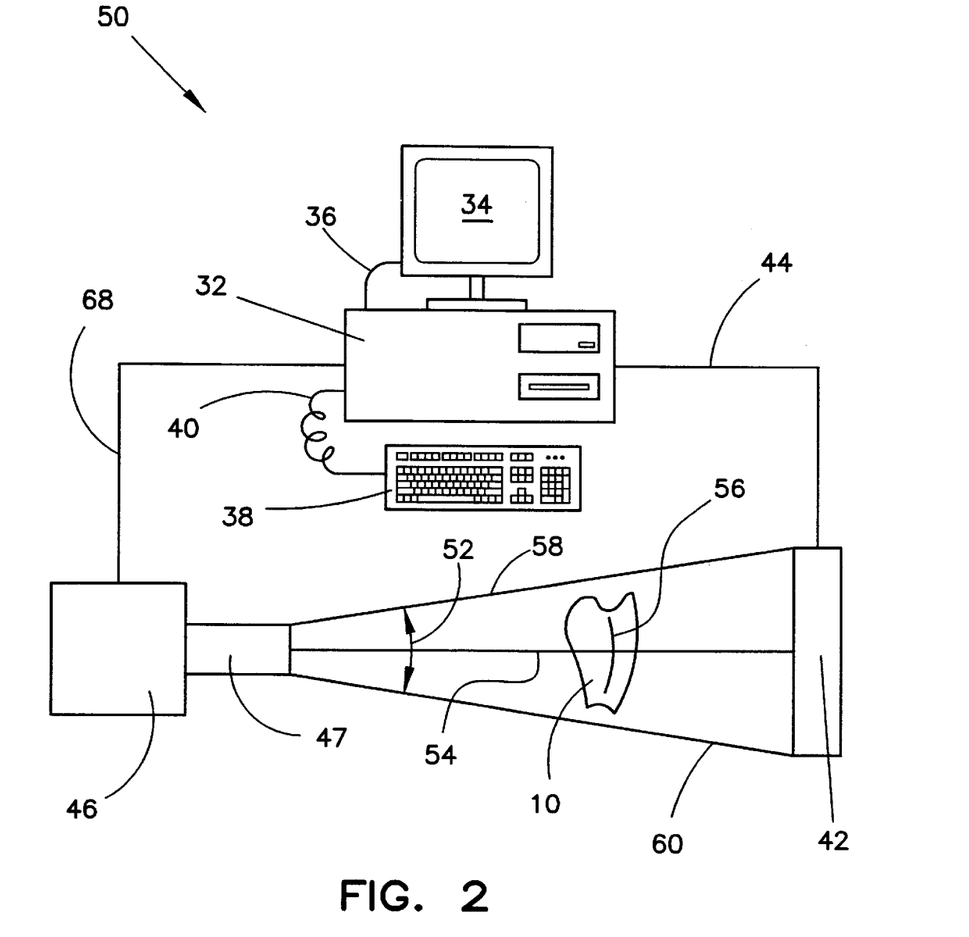
FIG. 2 is a diagrammatic representation of the various components and their interconnection utilized to carry out the method in accordance with the present invention.

Referring now to the drawings and, in particular FIG. 2, there is shown direct digital radiology (DDR) apparatus 50 used to carry out the present method in accordance with the principles of the present invention. DDR apparatus 50 includes computer 32 containing processing and memory circuitry such as is known in the art, that is in communication with keyboard or input device 38 via communication line 40 and in communication with display device 34 via communication line 36. Sensor or transducer 42 responsive to radiation is in communication with computer 32 via communication line 44. Sensor 42 is preferably responsive to X-ray radiation to digitally capture X-ray radiation as a radiograph (image) and is preferably an electronic sensor such as a charge-coupled device (CCD) as is known in the art. In this manner, sensor 42 replaces conventional X-ray film and allows for the almost instantaneous acquisition of X-rays. As well, such sensors utilize or need only 20% of the radiation necessary for traditional X-ray film in order to generate an image. While there are several major manufacturers of CCD sensors suitable for use with the present invention, two such manufacturers are 1) Schick Technologies, Inc. of Long Island, N.Y., and 2) Trex Trophy of Danbury, Conn. By utilizing an electronic sensor, root canal imaging can be measured with the accuracy close to the pixel size of the electronic sensor. The pixel size of the units used for implementation is approximately 45 microns. A measurement error of even an order of magnitude higher than the pixel size is acceptable for root canal treatment. Such accurate measurement allows the use of more precise canal instrumentation methods to improve root canal treatment.

Since the radiation is captured in digital form, computer 32 may easily process them. X-ray generator 46 as is known in the art is preferably in communication with computer 32 via communication line 68 although not necessarily so. Computer 32 may thus control the length of exposure time of X-rays from X-ray generator 46 necessary for sensor 42 to digitally capture an exposure, picture, or radiograph. As indicated, it may not be necessary for X-ray generator 46 to be in communication with computer 32 if X-ray generator 46 includes automatic exposure length timing. However, because of differences in types of sensors and/or the need to possibly adjust exposure times, computer 32 may provide the best control and be handled by the controlling software.

X-ray generator 46 is shown projecting X-rays depicted as lines emanating therefrom toward and through tooth 10 and onto sensor 42. The X-rays form a radiographic image onto the pixels of sensor 42 which can be modeled by an integrative perceptive projection by computer 32, where intensity of the signal (X-rays falling onto the pixels of the sensor) at every image point on the image plane is proportional (inversely) to radiographic absorption of the object element (tooth 10) along the direction of propagation (DOP), depicted in FIG. 2 as line 54. Sensor 42 defines an imaging or projection plane (image receptor) onto which the X-rays from X-ray generator 46 fall with point 56 preferably being the focal point. Angle 52, defined between rays 58 and 60, is the view angle for X-ray generator 46 relative to sensor 42.

The projection process is defined by the following equation:

$$p(x,y) = \int_{\vec{P}} f(x,y,z) d\vec{P}$$

where f (x, y, z) is the 3-D anatomy being imaged, p(x,y) is the projection image at projection plane (image receptor), and $\vec{P}$ 97 is the vector defining the direction of projection. $\vec{P}$ also defines the direction along which the integral is computed for all pixels on the image receptors. Knowing the (x ,y) coordinate of point $p_i$ on a given point of the image receptor (sensor 42) and direction of projection, one can define a line on 3-D space, $l_i$, emanating from $p_i$ along direction of propagation. Note that although this line extends on both sides of the image receptor, we will confine the analysis to the segment defined by the space between the image receptor and projection point. For every given set of points on the imaging plane, the set of 3-D lines will define a surface:

L={$P_i \forall$ =1,2 . . . , n}
S={$1_i \forall$ =1,2 . . . , n,$l_i$=$p_i$ at projection plane}

Figure 3:
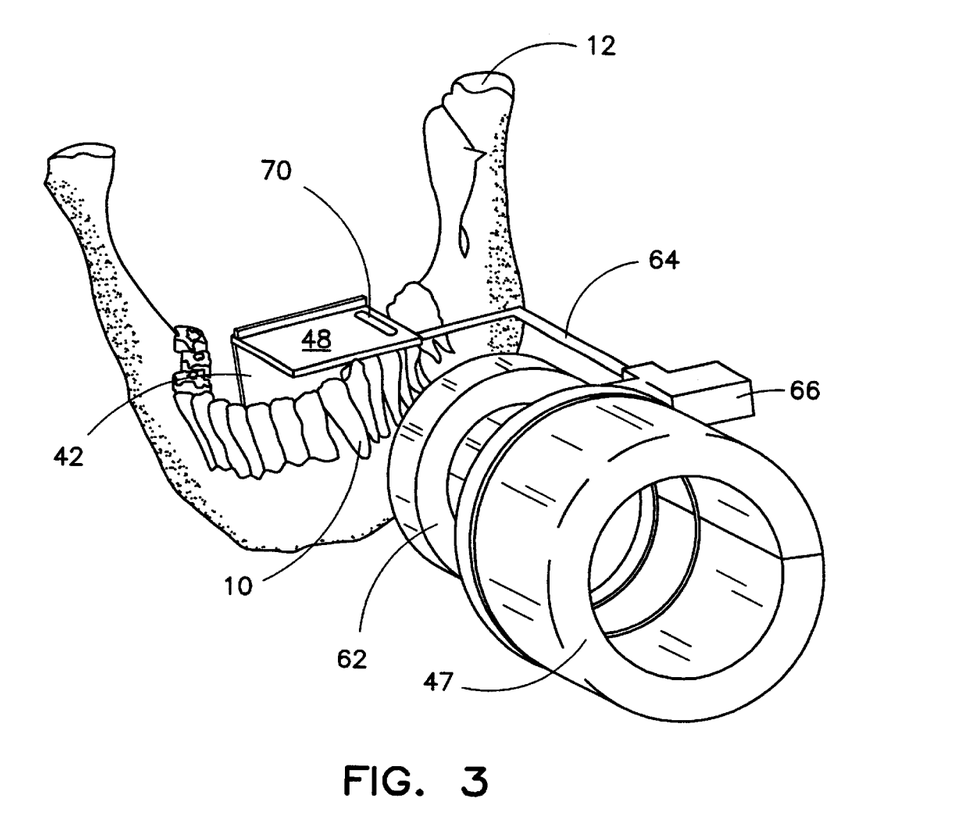
FIG. 3 is a front perspective view of a lower jawbone and teeth of a patient depicting the positioning of an X-ray head, aiming rod, ring, and X-ray sensor with respect to the lower jawbone in accordance with an aspect of the present invention.

With reference to FIG. 3, placement of x-ray cone or head 47 of X-ray generator 46 relative to jaw 12 is shown for obtaining a radiographic image of tooth 10 in order to determine the dimensions of its root canal in accordance with the principles of the present invention. Attached to X-ray cone 47 is ring 62 that is rotatable about X-ray cone 47. Coupled to ring 62 is attachment block 66 from which extends aiming rod 64. At an end of aiming rod 64 distal attachment block 66 is holder 48 that defines a bite block for the patient. It should be understood that holder 48 is shown larger than necessary for ease of understanding. Held by holder 48 is sensor 42 such that sensor 42 is within the mouth of the patient and behind tooth 10, generally perpendicular to holder 48. Aiming rod 64 helps maintain X-ray cone 47 in a fixed position and direction relative to sensor 42 during X-ray exposure. Holder 48, sensor 42 and aiming rod 64 are rotatable in preferably only two possible positions via a detent mechanism or the like. However, it should be understood that more angular positions may be possible including continuous angular changes. Holder 48 also preferably has an embedded metallic object 70 that is used as a reference during 3-D computation by computer 32 since a metallic object will readily show in an X-ray radiograph.

In order to carry out the present method, it is necessary to obtain at least two images or radiographs of the particular tooth of which the dimensions of the root canal are to be determined. In this regard, a first radiograph is taken at a first angular position at least in part according to the structure of aiming rod 64, attachment block 66, ring 62, and holder 48. Thereafter, a second radiograph is taken at a second angular position at least in part according to the structure of aiming rod 64, attachment block 66, ring 62, and holder 48 relative to the first radiograph.

Figure 4:
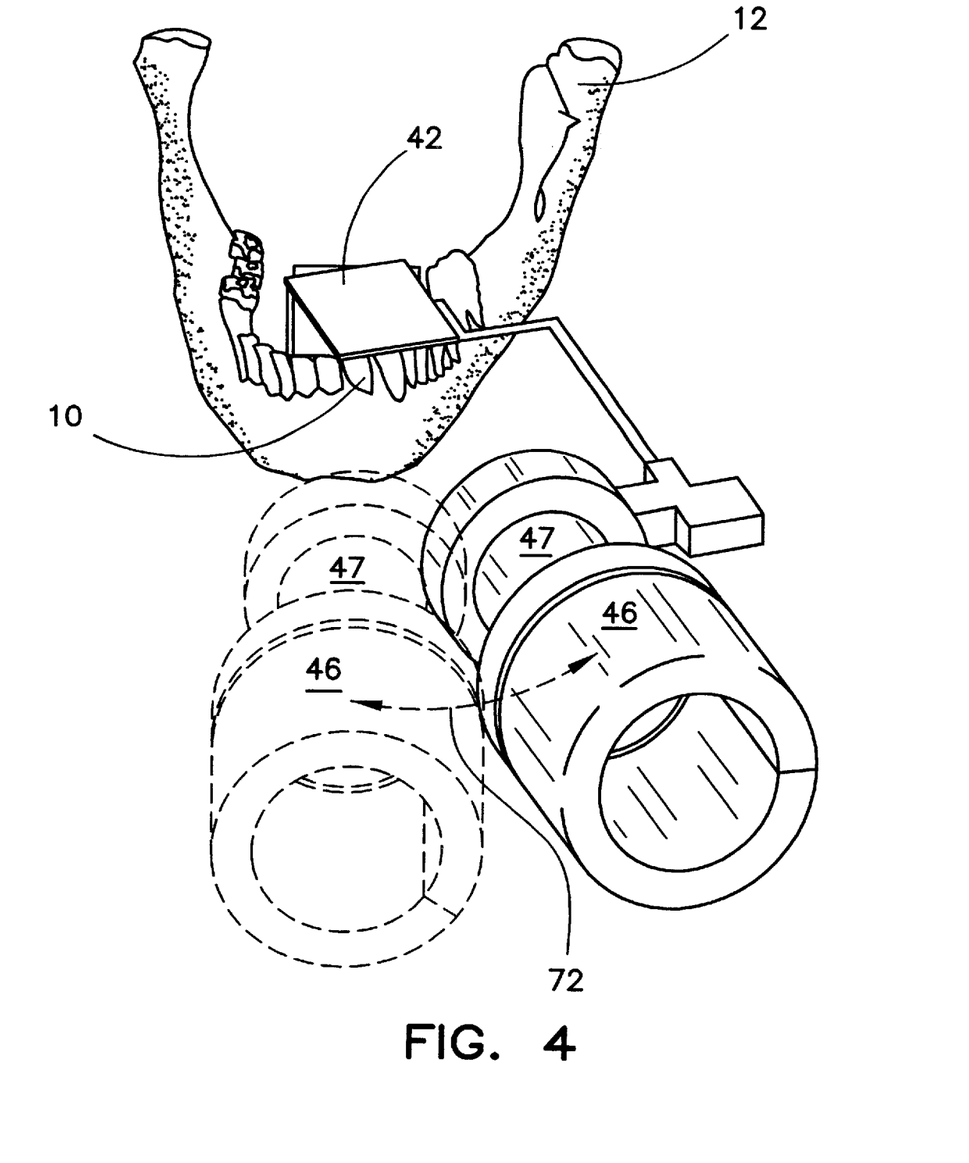
FIG. 4 is a diagram of the lower jawbone and teeth of the patient showing an exemplary positioning of the X-ray head to obtain a pair of radiographic images or stereo projection thereof in accordance with an aspect of the present invention.

FIG. 4 depicts the positioning of X-ray generator 46 relative to jaw 12 for obtaining the two projections. The two radiographs are taken at different angular positions at two locations by X-ray generator 46, the locations separated by an angular distance identified by arrow 72 in FIG. 4. It should be understood that the positions of X-ray generator 46 as shown in FIGS. 3 and 4 are representational only, and do not necessarily depict the actual placement of X-ray cone 47 relative to jaw 12 necessary for obtaining radiographs. It is only necessary that there be a preferable 5–40° separation between the two radiographic images, with 20° being a practical angular distance in clinical practice. The operator or clinician will follow typical placement of sensor 42 behind the tooth to be radiographed in the two positions so that there is one radiograph per position.

With respect to obtaining two radiographs, each at different angular positions relative to the tooth, aiming rod 64 provides two approaches in this regard. The first approach is through the use of a holder (48) that does not include an embedded object 70. Using this approach, the clinician or operator must provide the angular distance between each exposure to computer 32. In a second approach, embedded object 70 in holder 48 is proximate to the bite area (i.e. the place the patient is asked to bite to retain holder 48 in place). The radiographic images of object 70 in the two projections can be used to compute angular differences as well as any magnification involved in the process. From a clinical perspective, holder 48 will look and feel like common types of holders currently used, hence there is no need for a special procedure. Having metallic object 70 embedded in holder 48 necessitates an algorithm executable by computer 32 to locate the object and compute angular distance, but eliminates the need for the clinician to input the parameters manually, thus increasing the process and minimizing error.

Generally, once a radiograph is captured, two procedures are initiated by a computer program on computer 32. The first procedure, generally, is to detect the edges within the radiograph. This may be done automatically by computer 32 or manually by a user. The user is allowed to exclude edges in order to limit the process to the anatomy or object of interest, here the root canal. The second procedure, generally, is to use projection matrices to obtain or compute the 3-D surfaces of the tooth and/or root canal therein, depending on whether edges were excluded based on the detected edges. Once the 3-D surfaces of the anatomy of interest (e.g. the root canal) are obtained for each radiograph, the intersection of the surfaces from each radiograph will define the object of interest in 3-D space. After the 3-D object (e.g. root canal) is delineated and preferably displayed or imaged, the end user can calculate various aspects/dimensions of the root canal such as the length and curvature thereof.

Figure 5:
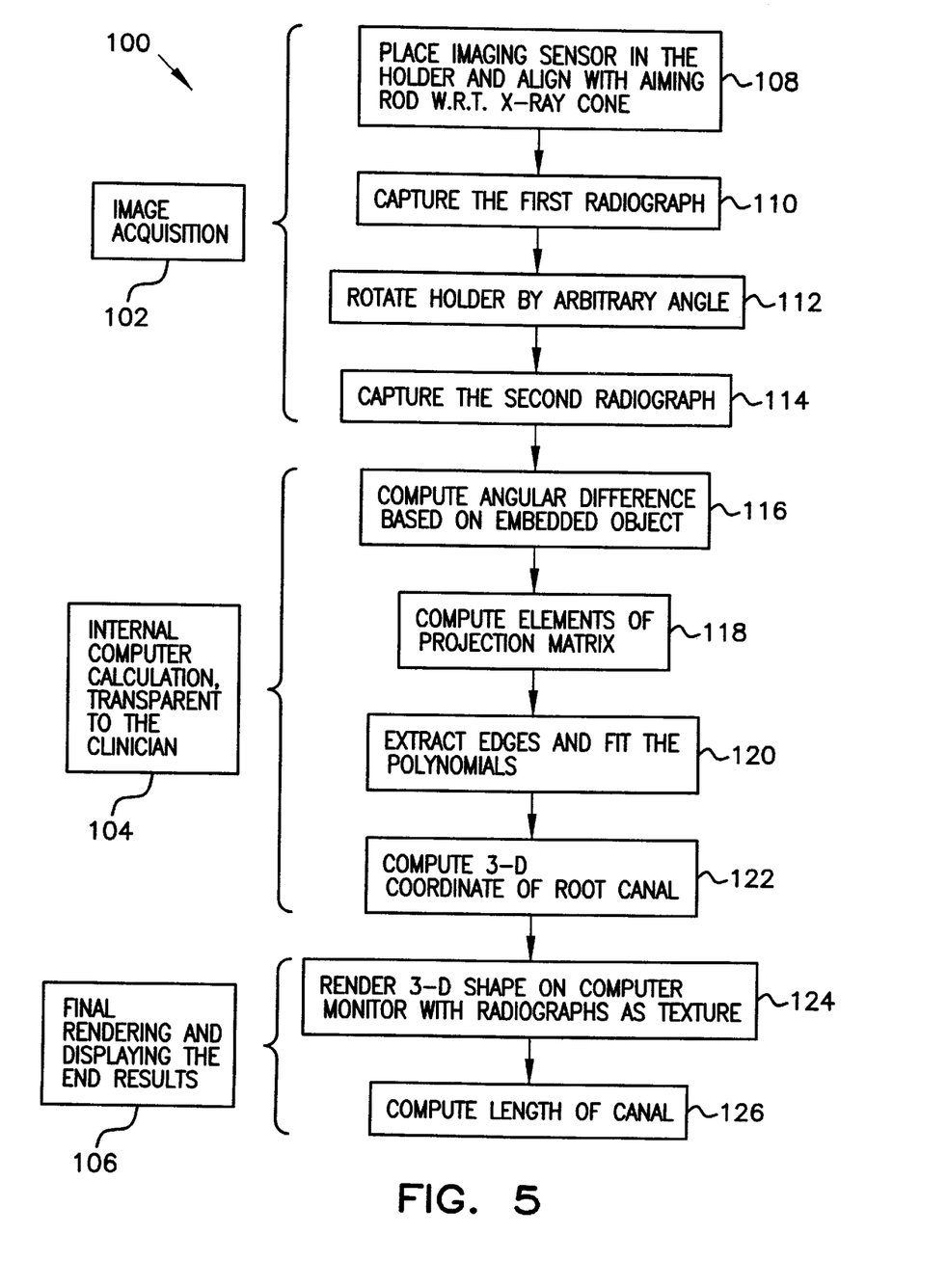
FIG. 5 is flowchart of the method in accordance with the present system.

With reference now to FIG. 5, there is shown flowchart 100 of the steps in accordance with the principles of the present invention for determining the dimensions of a root canal utilizing the apparatus shown and described herein. Generally, there is image acquisition 102 of the structure of the tooth. After such image acquisition 102, computer 32 performs necessary calculations 104 in accordance with a computer program to detect and surface compute the root canal. The image is displayable and ready for dimension calculation.

In particular, image acquisition 102 entails the placing of image sensor 42 within holder 48 of aiming rod 64 and aligning same with ring 62 to X-ray cone 47, relative to the tooth to be radiographed, step 108. After such alignment 108, the first radiograph is captured 110 on sensor 42 by allowing X-ray generator 46 to emit X-rays for a predetermined length of time dependent on the particular sensor used which is communicated to computer 32. After capture of the first radiograph 110, holder 48 is rotated by an arbitrary angle 112 via ring 62 and/or aiming rod 64. Thereafter, a second radiograph is obtained 114 in the same manner and communicated to computer 32. The digital images are electronically stored in computer 32, for manipulation/computation.

Once image acquisition 102 is complete, computer 32 performs its internal calculations 104. Specifically, the angular or angle distance between the first and second radiographs is computed preferably based on embedded object 70, 116. Alternatively, the angle or angular distance between the first and second radiograph may be inputted by the user utilizing demarcations (mechanical or visual) on the aiming rod 64. Then, the elements of the projection matrix are computed 118 if the projection matrix is not known or stored by the computer 32. In order to compute a 3-D shape from two projections or radiographs, a projection matrix must be computed. A projection matrix is a matrix that projects a 3-D object onto a 2-D plane. In other words, it is the process of image formation of a 3-D object into 2-D. The present algorithm for the projection matrix is based on parameters that are set during image acquisition. The parameters include 1) the relative distance between image sensor 42, bite-block 48 and X-ray cone 47, 2) X-ray cone 47 type and size, and 3) the relative angulation between the two radiographs. In the case of the relative distance between image sensor 42, bite-block 48 and X-ray cone 47, it is preferable that these distances are fixed and are thus read from the holder. In the case of the X-ray cone size 47, this is a fixed property of the type of X-ray cone and thus is a known quantity that can be entered during program execution or as a fixed constant written into the program if the X-ray cone size never varies. In the case of the relative angulation between the two radiographs, there are two approaches. One approach is to use a typical or regular sensor holder and aiming rod, and have a clinician provide an angular difference between each exposure as well as any other parameters as necessary. Another approach is to have the computer 32 perform the necessary calculations based on an object 70 that is embedded into bite block 48 of the aiming rod assembly. As the holder preferably has a three-dimensional metallic object 70 embedded in the bite block 48, the radiographic images will show the object 70. The dimensions of the object 70 are known by the computer 32 and thus may be used to compute angular differences between the two radiographs, as well as the magnification of the radiographs. Having the embedded metallic object 70 eliminates the need for the manual input of the parameters for the computation of the projection matrices. A projection matrix for each image needs to be computed.

After computation of the projection matrices, 118, generally edges are identified and fit into polynomials, 120 to define surfaces of the tooth (e.g. the root canal). Specifically, edges within each radiograph are automatically detected. However, this may be accomplished with user input. In accordance with the present invention, edge detection is accomplished in several substeps of which not all may be done, namely: a) noise is minimized by pre-filtering the radiograph; b) dead and overexposed pixels are located within each radiograph by searching and replacing with the mean gray level of neighboring pixels; c) median filtering is performed; d) threshold selection for segmenting the dental radiograph (i.e. extracting the form of the root canal) is accomplished by computing a single threshold for the entire image which will define the surfaces of various objects (e.g. the root canal) of the tooth by the edges; e) a central line of the root canal is obtained using a morphological skeleton; and f) the root canal is modeled by an $n^{th}$ order polynomial. The edges are then molded as surfaces or contours. Once the surfaces are computed as above, they are passed to the next stage. The 3-D coordinates of the root canal can then be obtained 122 by taking the intersection of the surfaces from each radiograph.

Last, the final rendering (imaging) and display 106 is accomplished. Specifically, the 3-D shape of the root canal from the intersection computation is rendered on computer display 34 with radiographs as texture 124. Thereafter, the dimensions such as length of the root canal is computed 126. Length, for example, is accomplished by summing the Euclidean distance between the end points of the tooth (i.e. sum of the distance between consecutive voxels). The clinician has the choice of marking the beginning and end of the root canal. Similarly, the end user can select the entire length or parts thereof of the 3-D model for length and curvature computation.

It should be understood that not all of the above steps are necessary in order to image the root canal and/or determine the dimensions thereof. Some steps are general and necessary, while other steps are specific to the general steps and may be accomplished and/or done in another manner.

Implementation of the present system is accomplished in a user-friendly software program incorporating the various elements and features described above. Such implementation is accomplished in real time, which helps accelerate the transfer of knowledge from research into practice. As an example, such a program is presented below.

```
/* Include Files*/
#include <iostream.h>
#include "vtk.h"
#include "vtkRenderWindow.h"
#include "vtkRenderWindowInteractor.h"
#include "vtkActor.h"
#include "vtkCylinderSource.h"
#include "vtkPolyDataMapper.h"
#include "vtkCylinderSource. h"
#include "vtkCamera.h"
#include "vtkImager.h"
#include "vtkImageWindow.h"
#include "vtkPolyDataMapper.h"
#include "vtkCamera.h"
#include "vtkAxes.h"
#include "vtkBMPReader.h"
#include "vtkObjReader.h"
//#define WHAT_TIS
#define NumInt 980
#define Tval 14
#define SIZEX 760
#define SIZEY 524
class volVal
    {
    public:
        float minx, miny, maxx, maxy;
        float posx, posy, posz;
    };
typedef struct {
    double x,y,z;
    } XYZ;
void myViewToWorld (float &, float &, float &, vtkMatrix4x4);
void myDisplayToView (float &, float &, float &, int, int);
void myWorldToView (vtkPoints *, vtkMatrix4x4 *);
void GenerateThePoints (char *, int, int);
float ComputeTotalDistance (vtkPoints *);
float Dist2Pts (float *point1, float * point2)
    {
    float Distance;
    Distance = sqrt((point1[0]-point2[0])*(point1[0]-point2[0])+
            (point1[1]-point2[1])*(point1[1]-point2[1])+
            (point1[2]-point2[2])*(point1[2]-point2[2]));
    return Distance;
    }
// ProjectionMatrixComputation (position, parallel_scale);
```

```
void ProjectionMatrixComputation (float, int, float, char *);
float *IntersectTwoLines (vtkLineSource *, vtkLineSource *, bool *);
int LineLineIntersect (vtkLineSource *, vtkLineSource *, float *);
void ACall (char *, char *);
float GetMagnification (char *, float);
ofstream fout ("chumma.txt");
void main ()
    {
    char fname[7], fname1[7];
    char *file1, file2[7];
    int angle1, angle2;
    file1 = new char [7];
    while (true)
        {
        cout << "Input File 1";
        cin > >file1;
        cout << "Input File 2";
        cin > >file2;
        strcpy (fname, file1);
        strcpy (fname1, file2);
        float k = GetMagnification ("mag.txt", 14.5);
        strcpy (fname, file1);
        strcpy (fname1, file2);
        angle1 = atoi(file1);
        angle2 = atoi(file2);
        fout <<angle<<" "<<angle2<<" ";
        /* ProjectionMatrixComputation (14.5, angle1, k, fname);
        ProjectionMatrixComputation (14.5, angle2, k, fname1);
        strcpy (fname, file1);
        strcpy (fname1, file2);
        GenerateThePoints (fname, SIZEX, SIZEY);
        GenerateThePoints (fname1 , SIZEX, SIZEY);*/
        strcpy (fname, file1);
        strcpy (fname1, file2);
        ACall (fname, fname1);
        }
    fout.close ();
    return;
    }
// This function does Interpolation over the values
// and returns the magnification
float GetMagnification ( char *fname, float x )
    {
    float xval[9], yval[9];
    float y;
    float dif, dift;
    float c[9],d[9];
    int ns = 1, m;
    ifstream nfile (fname);
    for (int i=1;i<=8;i++)
        {
        nfile >>xval[i]>>yval[i];
        c[i] = yval[i];
        d[i] = yval[i];
        }
    dif = fabs (x - xval[1]);
    for (i = 1;i<=8;i++)
        {
        if((dift = fabs (x-xval[i])) <dif)
            {
            ns = i;
            dif = dift;
            }
        }
    float ho, hp, w, den, dy;
    y = yval [ns-- ];
    for ( m= 1;m<8;m++)
        {
        for (i=1;i<=8-m;i++)
            {
            ho = xval[i]-x;
            hp = xval[i+m]-x;
            w= c[i+1]-d[i];
            if ((den = ho-hp) == 0.0)
                {
                cout <<"Error"<<end1;
                break;
                }
            den = w/den;
            d[i] = hp*den;
            c[i] = ho*den;
            }
        y += (dy=(2*ns < (8-m) ) ? c[ns+ 1] : d[ns-- ]);
        }
    return y;
    }
void ProjectionMatrixComputation(float distance,
int angle, float scale, char *filename)
    {
    double pi = 3.1415926535;
    float pos[3];
    pos[2] = distance * cos (angle * pi/180.0);
    pos[1] = 0.0;
    pos[0]= distance * sin (angle *pi/180.0);
    strcat (filename, ".val");
    ofstream file (filename);
    vtkMath math;
    vtkIndent ind = 0;
    vtkRenderer *aren = vtkRenderer::New();
    vtkRenderWindow * renWin = vtkRenderWindow::New();
    renWin-> AddRenderer( aren );
    vtkRenderWindowInteractor *iren =
    vtkRenderWindowInteractor::New();
    iren-> SetRenderWindow( renWin );
    renWin->SetSize (SIZEX, SIZEY);
    vtkMatrix4x4 *projmat1;
    float vp[3];
    vtkCamera *aCamera = vtkCamera::New();
    aCamera->ParallelProjectionOn ();
    aCamera->SetParallelScale (scale);
    aCamera->SetFocalPoint (0.0, 0.0, 0.0);
    aCamera->SetPosition (pos);
    aren-> SetActiveCamera( aCamera );
    aCamera->ComputeViewPlaneNormal ();
    aCamera->ComputeViewTransform ();
    aCamera->ComputePerspectiveTransform ( 1.0, 0, 0, 1.0);
    aCamera->SetClippingRange (0.01, 1.01);
    projmat 1 = aCamera->GetCompositePerspectiveTransformMatrix
    (1.0, 0.0, 1.0);
    aCamera->GetViewPlaneNormal (vp);
    //cout<<"ViewPlaneNormal"
    <<vp[0]<<" "<<vp[1]<<" "<<vp[2]<<end1;
    file<<vp[0]<<" "<<vp[1]<<" "<<vp[2]<<end1;
    file <<scale <<end1;
    for (int i=0;i<4;i++)
        {
        for (int j=0;j<4;j++)
            {
    //      cout < <projmat1->GetElement (i,j)< <" ";
            file<<projmat1->GetElement (i,j)<<" ";
        }
    file< <end1;
    //cout<<end1;
    }
    projmat1->Delete ();
    /*aCamera->Delete ();
    ren Win->Delete ();
    aren->Delete ();
    iren->Delete ();*/
    file.close ();
    }
void GenerateThePoints ( char filename[7], int sizex, int sizey)
    {
    char outfile[20];
    char myfile [20];
    char txtfile [20];
    bool set = false;
    strcpy (outfile, filename );
    strcpy (myfile, filename);
    strcpy (txtfile, filename);
    strcat (outfile, ".pts");
    strcat (filename, "-edge2.bmp");
    strcat (txtfile, ".txt");
    strcat(myfile, ".myt");
    ofstream file(outfile);
    ofstream mfile (myfile);
    ifstream TXTfile (txtfile);
    vtkImager *aren = vtkImager::New();
```

-continued

```
unsigned char *rgbs, *tmp;
vtkImageWindow *renWin = vtkImageWindow::New();
renWin->AddImager(aren);
renWin->DebugOn ();
vtkBMPReader *bmpfile =vtkBMPReader::New ();
bmpfile->SetFileName (filename);
bmpfile->Update ();
vtkImageMapper *map = vtkImageMapper::New ();
map->SetInput (bmpfile->GetOutput ());
vtkActor2D *actor = vtkActor2D::New ();
actor->SetMapper (map);
aren->AddActor2D( actor );
renWin->SetSize (sizex, sizey);
renWin->Render ();
// renWin->Render ();
rgbs = renWin->GetPixelData (0,0, sizex-1, sizey-1,1);
tmp = rgbs;
float z=1.0;
float x1, y1;
int x,y;
/* while (!TXTfile.eof() )
    {
        TXTfile >>y >>x;
        y1 = (float)x;
        x1 = (float)y;
        aren->LocalDisplayToDisplay (x1, y1);
        aren->DisplayToNormalizedDisplay (x1, y1);
        aren->NormalizedDisplayToViewport (x1 ,y1);
        aren->ViewportToNormalizedViewport (x1, y1);
        aren->NormalizedViewportToView (x1, y1, z);
//         aren->ViewToWorld (x1, y1, z);
        mfile <<" "<<x1 <<" "<<y1<<" "<<z;
    }
*/
for (y = 0;y < sizey;y++)
    {
        for (x = 0 ; x < sizex;x++)
            {
                if ((tmp [0] && tmp [1] && tmp [2])&& !( set))
                {
                    z = 1.0;
                    file << x <<" " << y << end1;
                    X1 = y;
                    y1 = x;
                    aren->DisplayToNormalizedDisplay (x1, y1);
                    aren->NormalizedDisplayToViewport (x1, y1);
                    aren->ViewportToNormalizedViewport (x1, y1);
                    aren->NormalizedViewportToView (x1, y1, z);
//                  aren->ViewToWorld (x1, y1, z);
                    mfile <<" "<<x1 <<" "<<y1<<" "<<z;
//                  set = true;
                }
                tmp +=3;
            }
        set = false;
    }
actor->Delete ();
bmpfile->Delete ();
renWin->Delete ();
map->Delete ();
aren->Delete ();
file.close ();
mfile.close ();
TXTfile.close ();
return;
}
void ACall(char *filename, char *filename1)
{
volVal test, test1;
char valfile[20], valfile1[20];
char nfile [20];
strcpy (valfile, filename);
strcpy (valfile1, filename1);
strcat (valfile, ".val");
strcat (valfile1, ".val");
strcpy (nfile,filename);
strcat (nfile, "-");
strcat (nfile, filename1);
strcat (nfile, ".pts");
```

-continued

```
int angle1, angle2;
angle1 = atoi(filename);
angle2 = atoi (filename1);
char ptsfile[20], ptsfile1[20];
strcpy (ptsfile, filename);
strcpy (ptsfile1, filename1);
strcat (ptsfile, ".myt");
strcat (ptsfile1, ".myt");
char pntfile[20], pntfile1[20];
strcpy (pntfile, filename);
strcpy (pntfile1, filename1);
strcat (pntfile, ".pnt");
strcat (pntfile1, ".pnt");
ifstream file(valfile);
ifstream file1 (valfile1);
ifstream pts (ptsfile);
ifstream pts1 (ptsfile1);
ofstream out (pntfile);
ofstream out1 (pntfile1);
ofstream nout (nfile);
float temp, temp1;
float x [3];
vtkMatrix4x4 mat, mat1;
vtkIndent ind = 0;
vtkFloatPoints *point1 = vtkFloatPoints::New ();
vtkFloatPoints *point2 = vtkFloatPoints::New ();
vtkFloatPoints *point = vtkFloatPoints::New ();
vtkFloatPoints *dispts = vtkFloatPoints::New ();
vtkFloatPoints *dispts1 = vtkFloatPoints::New ();
float scale, scale1;
file > > test.posx > > test.posy > >test.posz;
file1 >>test1.posx >> test1.posy >>test1.posz;
file> >scale;
file1> >scale1;
int j;
float testvalx[2],teskvaly[2];
for ( int i =0;i<4;i++)
    {
        for (j=0;j<4;j++)
            {
                file >> temp;
                file1 >> temp1;
                mat.SetElement (i,j,temp);
                mat1.SetElement (i,j,temp1);
            }
    }
// now after the data input main processing..
// using the assumption that we are having lines in the system
// let us try to find set of points
// converting everything to view-co-ordinates from display 640x480
float I,m,n;
i=0;
j=0;
point1 ->Reset ();
while (!pts.eof())
    {
        n = 0.0;
        pts >>I>>m>>n;
        dispts->InsertNextPoint (I,m,n);
    }
// Compute the Distance between the points and
// find D
// Interpolating on Data
// Whole Distance
// Now we need to store all the individual distances in
// an array of float so that easy lookup can be achieved
cout<<"Number of points in
Image1" <<dispts->GetNumberOfPoints ()<<end1;
float nxtpt [3];
float pt1[3]:
vtkLineSource *lines1[2000];
vtkLineSource *lines2[2000];
for (i = 0;i< dispts->GetNumberOfPoints ();i++)
    {
        lines1[i] = vtkLineSource::New ();
        dispts->GetPoint (i,pt1);
        myViewToWorld (pt1[0],pt1[1],pt1[2],mat);
        out <<" "<<pt1[0]<<" "<<pt1[1]<<" "<<pt1[2]<<end1;;
        nxtpt [0] = pt1[0] + test.posx * (Tval-40);
```

-continued

```
        nxtpt [1] = pt1[1] + test.posy * (Tval-40);
        nxtpt [2] = pt1[2] + test.posz * (Tval-40);
        lines1 [i]->SetPoint1 (nxtpt[0], nxtpt[1], nxtpt[2]);
        nxtpt [0] = pt1[0] + test.posx * Tval;
        nxtpt [1] = pt1[1] + test.posy * Tval;
        nxtpt [2] = pt1[2] + test.posz * Tval;
        lines1 [i]->SetPoint2 (nxtpt[0], nxtpt[1], nxtpt[2]);
        lines1 [i]->SetResolution (5);
    }
while (!pts1.eof())
    {
        pts1 >>l>>m>>n;
        dispts1 -> InsertNextPoint (l,m,n);
    }
cout<<"Number of points in
Image2" <<dispts1->GetNumberOfPoints ()<<end1;
for (i = 0;i< dispts1->GetNumberOfPoints ();i++)
    {
        dispts1->GetPoint (i,pt1);
        myViewToWorld (pt1[0],pt1[1],pt1[2],mat1);
        out1<<" "<<pt1[0]<<" "<<pt1[1]<<" "<<pt1[2]<<end1;
        nxtpt [0] = pt1[0] + test.posx * (Tval-40);
        nxtpt [1] = pt1[1] + test.posy * (Tval-40);
        nxtpt [2] = pt1[2] + test.posz * (Tval-40);
        lines2 [i] = vtkLineSource::New ();
        lines2 [i]->SetPoint1 (nxtpt[0], nxtpt[1], nxtpt[2]);
        nxtpt [0] = pt1[0] + test.posx * Tval;
        nxtpt [1] = pt1[1] + test.posy * Tval;
        nxtpt [2] = pt1]2] + test.posz * Tval;
        lines2 [i]->SetPoint2 (nxtpt[0], nxtpt[1], nxtpt[2]);
    }
bool result=false;
float xx[4];
i=0;
int spt1, spt2,tmp;
spt1 = dispts->GetNumberOfPoints ()-1;
spt2 = dispts1->GetNumberOfPoints ()-1;
bool setbool = false;
if (spt1 > spt2)
    {
        tmp = spt2;
        spt2 = spt1;
        spt1 = tmp;
        setbool = true;
    }
bool newset = false;
float lowval = 100000.00000;
int mm, nn;
    for (i=0;i <=spt1 ;i++)
    {
    for (j=0;j<=spt2;j++)
        {
        if (setbool)
            {
            if (LineLineIntersect(lines1[j], lines2[i],xx))
                {
                if (xx[3] < lowval )
                    {
                    x[0] = xx[0];x[1]=xx[1];x[2] = xx[2];
                    lowval = xx[3];
                    newset = true;
                    mm =i;
                    nn = j;
                    //fout <<xx[0]<<" "<<xx[1]<<" xx[2]<<end1;
                    //point->InsertNextPoint (x);
                    //fout <<i <<" "<<j<<" "xx[3]<<end1;
                    //fout <<xx[3]<<end1;
                    //break;
                    }
                }
            }
        else
            {
            if(LineLineIntersect (linesl[i], lines2[j], xx))
                {
                if (xx[3] < lowval)
                    {
                    x[0] = xx[0];x[1]=xx[1];x[2] = xx[2];
                    lowval = xx[3];
```

-continued

```
                    newset = true;
                    mm=i;
                    nn = j;
                    //fout <<XX[0]<<" "xx[1]<<" "xx[2]<<end1;
                    //point->InsertNextPoint (x);
                    //fout <<i<<" "<<j<<" "<<xx[3]<<end1;
                    //fout <<xx[3]<<end1;
                    //break;
                    }
                }
            }
        }
    }
if (newset)
    {
        point-> InsertNextPoint (x);
        nout<<x[0] <<" "<<x[1]<<" "<<x[2]<<" "
            <<lowval<<"@"<<mm<<" "<<nn<<
            end1;
    }
    lowval = 10000.00000;
    newset = false;
    }
cout<<"Number of Intersecting
Points"<<point->GetNumberOfPoints ()<<end1;
/*if (point->GetNumberOfPoints () == 0)
    exit (1);*/
fout <<point->GetNumberOfPoints ()<<" ";
cout <<"Length of the rootCanal in World
Co-ords"<<ComputeTotalDistance (point)< <end1;
fout < <ComputeTotalDistance (point)< <end1;
/*vtkRenderer *aren = vtkRenderer::New();
vtkRenderWindow *renWin = vtkRenderWindow::New();
renWin-> Add Renderer( aren );
vtkRenderWindowInteractor *iren = vtkRenderWindowInteractor::New();
iren-> SetRenderWindow( renWin );
vtkPolyData *adata3 = vtkPolyData::New ();
adata3->SetPoints (point);
adata3->Update ();
vtkPolyData *adata4 = vtkPolyData::New ();
adata4->SetPoints (dispts );
vtkPolyData *adata5 = vtkPolyData::New ();
adata5->SetPoints (dispts1 );
vtkAppendPolyData *adata1 = vtkAppendPolyData::New ();
for (i=O;i<dispts->GetNumberOfPoints ()-1;i++)
    adata1->AddInput (lines1[i]->GetOutput ());
adata1->Update ();
vtkAppendPolyData *adata2 = vtkAppendPolyData::New ();
for (i=0;i<dispts1->GetNumberOfPoints ()-1;i++)
    adata2->AddInput (lines2[i]->GetOutput ());
adata2->Update ();
vtkPolyDataMapper *mapper1 = vtkPolyDataMapper::New ();
mapper1->SetInput (adata1->GetOutput ());
mapper1->ScalarVisibilityOff();
vtkActor *actor1 = vtkActor::New ():
actor1->SetMapper (mapper1);
actor1->GetProperty ()->SetColor (0.5,0.5,0.5);
vtkPolyDataMapper *mapper2 = vtkPolyDataMapper::New ();
mapper2->SetInput (adata2->GetOutput ());
vtkActor *actor2 = vtkActor::New ();
actor2->SetMapper (mapper2);
vtkSphereSource *sphere = vtkSphereSource::New ();
sphere->SetRadius (0.01);
sphere->SetThetaResolution(2); sphere-> SetPhiResolution(2);
vtkGlyph3D *glyph = vtkGlyph3D::New ();
glyph->SetInput (adata3);
glyph->SetSource(sphere->GetOutput ());
glyph->SetScaleFactor (1.0);
vtkPolyDataMapper *mapper = vtkPolyDataMapper::New ();
mapper->SetInput (glyph->GetOutput ());
mapper->ScalarVisibilityOff ();
vtkActor *actor= vtkActor::New ();
actor->SetMapper (mapper);
vtkAxes *axes = vtkAxes::New();
axes->SetOrigin(0,0,0);
axes->SetScaleFactor(2);
vtkTubeFilter *axesTubes = vtkTubeFilter::New();
axesTubes-> SetInput(axes->GetOutput());
axesTubes-> SetRadius(0.01);
axesTubes-> SetNumberOfSides(6);
```

-continued

```
vtkPolyDataMapper *axesMapper = vtkPolyDataMapper::New();
axesMapper->SetInput(axesTubes-> GetOutput());
vtkActor *axesActor = vtkActor::New ();
axesActor->SetMapper (axesMapper);
// int id;
aren->AddActor (actor);
// aren->AddActor (actor3);
// aren->AddActor (actor4);
    // aren->AddActor (actor1);
    // aren->AddActor (actor2);
    aren->AddActor (axesActor);
    // aren->AddActor (actorobj);
    ren Win->Render();
    // aren->SetBackground (1,1,1);
    iren->Start();*/
    file.close ();
    file1.close ();
    pts.close ();
    pts1.close ();
    out.close ();
    out1.close ();
    //point1->Delete ();
    //point2->Delete ();
    //dispts->Delete ();
    //dispts1->Delete ();
    //point->Delete ();
    for (j=0;j<dispts->GetNumberOfPoints ()-1;j++)
        lines1[j]->Delete ();
    for (j=0;j<dispts1->GetNumberOfPoints ()-1;j++)
        lines2[j]->Delete ();
// fclose (factor);
}
#define EPS 0.001
#define ABS(x) ((x) < 0 ? -(x) : (x))
int LineLineIntersect( vtkLineSource *line1,
vtkLineSource *line2, float *retval)
    {
    float *pp1, *pp2, *pp3 , *pp4;
    XYZ p1, p2, p3, p4, pa, pb;
    double mua, mub;
    XYZ p13,p43,p21;
    double d1343,d4321,d1321,d4343,d2121;
    double numer,denom;
    pp1 = line1->GetPoint1 ();
    pp2 = line1->GetPoint2();
    pp3 = line2->GetPoint1();
    pp4 = line2->GetPoint2 ();
    p1.x = pp1[0];p1.y = pp1[1];p1.z = pp1[2];
    p2.x = pp2[0];p2.y = pp2[1];p2.z = pp2[2];
    p3.x = pp3[0];p3.y = pp3[1];p3.z = pp3[2];
    p4.x = pp4[0];p4.y = pp4[1];p4.z = pp4[2];
    p13.x = p1.x - p3.x;
    p13.y = p1.y - p3.y;
    p13.z = p1.z - p3.z;
    p43.x = p4.x - p3.x;
    p43.y = p4.y - p3.y;
    p43.z = p4.z - p3.z;
    if (ABS(p43.x) < EPS && ABS(p43.y)
    < EPS && ABS(p43.z) < EPS)
        return(FALSE);
    p21.x = p2.x - p1.x;
    p21.y = p2.y - p1.y;
    p21.z = p2.z - p1.z;
    if (ABS(p21.x) < EPS && ABS(p21.y)
    < EPS && ABS(p21.z) < EPS)
        return(FALSE);
    d1343 = p13.x * p43.x + p13.y * p43.y + p13.z * p43.z;
    d4321 = p43.x * p21.x + p43.y * p21.y + p43.z * p21.z;
    d1321 = p13.x * p21.x + p13.y * p21.y + p13.z * p21.z;
    d4343 = p43.x * p43.x + p43.y * p43.y + p43.z * p43.z;
    d2121 = p21.x * p21.x + p21.y * p21.y + p21.z * p21.z;
    denom = d2121 * d4343 - d4321 * d4321;
    if (ABS(denom) < EPS)
        return (FALSE);
    numer = d1343 * d4321 - d1321 * d4343;
    mua = numer / denom;
    mub = (d1343 + d4321 * (mua)) / d4343;
    pa.x = p1.x + mua * p21.x;
    pa.y = p1.y + mua * p21.y;
    pa.z = p1.z + mua * p21.z;
    pb.x = p3.x + mub * p43.x;
    pb.y = p3.y + mub * p43.y;
    pb.z = p3.z + mub * p43.z;
    float x = pa.x-pb.x;
    float y = pa.y-pb.y;
    float z = pa.z-pb.z;
    retval[3] = sqrt( x*x+y*y +z*z);
    if (retval[3]< EPS)
        {
        retval[0] = pa.x;
        retval[1] = pa.y;
        retval[2] = pa.z;
        }
    else
        return FALSE;
    return TRUE;
    }
void myViewToWorld (float &x, float &y, float &z, vtkMatrix4x4 mat)
    {
    float result [4];
    result [0]= x;
    result [1]= y;
    result [2]= z;
    result [3]= 1.0;
    mat.Invert ();
    mat.Transpose ();
    mat.PointMultiply (result, result);
    if (result [3])
        {
        x = result [0] = result [0]/ result [3];
        y = result [1] = result [1]/ result [3];
        z = result [2] = result [2]/ result [3];
        }
    }
void myDisplayToView (float &x, float &y, float &z , int sizex, int sizey)
    {
    // int sizex, sizey;
    // Display to NormalizedDisplay
    // sizex = SIZEX;
    // sizey = SIZEY;
    float vp[4];
    vp[0]= 0;
    vp[1]= 0;
    vp[2]= 1;
    vp[3]= 1;
    // converting localDisplay To Display
    // y = sizey - y - 1;
    if (sizex> 1)
        x = x / (sizex - 1);
    else
        x = 0.0;
    if (sizey > 1)
        y = y / (sizey - 1);
    else
        y = 0.0;
    // This is Normalizeddisplay to Viewport
    x = x - vp[0];
    y = y - vp[1];
    x = x*(sizex-1);
    y = y*(sizey-1);
    // ViewPort to NormalizedViewPort
    if (sizex> 1)
        {
        x = x / (sizex - 1);
        }
    else
        {
        x = 0.0;
        }
    if (sizey > 1)
        {
        y = y / (sizey - 1);
        }
    else
        {
        y = 0.0;
        }
    x = x / (vp[2] - vp[0]);
```

```
            y = y / (vp[3] - vp[1]);
            // NormaliledViewPort to View
            x = (2.0*x - 1.0)*(float)sizex/(float)sizey;
            y = (2.0*y - 1.0)*1.0;
}
// this part of the code is for measuring purposes..
// convert every intersection point from World To View..
// then in View Measure the Lengths of Line.. with this
length the ratio can be predicted..
void myWorldToView (vtkPoints *points, vtkMatrix4x4 *mat)
        {
        float view[4];
        float end1[3], end2[3];
        int endind1, endind2;
        float mx[3], my[3];
        float distance = -1000000.0, ndist;
        int i,j;
        float *x;
        x = new float [4];
        vtkPoints *v point = vtkPoints::New ();
        for (i=0;i<points->GetNumberOfPoints ()-1;i++)
            {
            points->GetPoint (i, x);
            view[0] = x[0]*mat->
                Element[0][0] + x[1]*mat->Element[0][1] + x[2]*mat-
>Element[0][2]
                    + mat->Element[0][3];
            view[1] = x[0]
                *mat->Element[1][0] + x[1]*mat->Element[1][1] + x[2]*mat-
>Element[1][2]
                    + mat->Element[1][3];
            view[2] = x[0]*mat->Element[2][0] + x[1]
                *mat->Element[2][1] + x[2]*mat-
>Element[2][2]
                    + mat->Element[2][3];
            view[3] = x[0]*mat->Element[3][0] + x[1]
                *mat->Element[3][1] + x[2]*mat-
>Element[3][2]
                    + mat->Element[3][3];
            if (view[3] ! = 0.0)
                {
                x[0]= view[0]/view[3];
                x[1]= view[1]/view[3];
                x[2]= view[2]/view[3];
                }
            v point-> InsertNextPoint (x);
            }
for (i=0;i<vpoint->GetNumberOfPoints ()-2;i++)
{
    vpoint->GetPoint (i, mx);
    for (j=i+1;j<vpoint->GetNumberOfPoints ()-1;j++)
        {
        vpoint->GetPoint (j,my);
        ndist = Dist2Pts (mx, my);
        if (ndist > distance)
            {
            distance = ndist;
            endind1 = j;
            endind2 = i;
            }
        }
}
vpoint->GetPoint (endind1, end1);
vpoint->GetPoint (endind2, end2);
cout<<"Distance in view Frame"<<distance<<end1;
mat->Delete();
}
float ComputeTotalDistance (vtkPoints *pts)
{
    int k = pts->GetNumberOfPoints ();
    float mx[3], my[3];
    float totdist = 0.0;
    float m=10000.000;
    float loval = 10000.000;
    for (int i=0;i<k-1;i++)
    {
        pts->GetPoint (i,mx);
        for (int j = i+1;j<k;j++)
        {
        if (i!=j)
        {
            pts->GetPoint (j,my);
            loval = Dist2Pts (mx,my);
            if(m > loval)
                {
                m = loval;
                }
        }
        }
        totdist+=m;
        m = 10000.000;
    }
    return totdist;
}
```

The present system also may provide for an objective and accurate method for identifying and classifying tooth root resorption and its progress. The present system with its concurrent imaging processing techniques, can also be used to better visualize and detect root fractures, accessory canals, their length and directions. Additionally, the present system provides clinical and outcome assessment for efficacy of new techniques for various instrumentation techniques. In this regard, the present system can be used as a non-destructive "gold standard" in such studies. As well, reconstructed 3-D root canals using this method, along with radiographic images can be used for innovative computer-based training modules by simulating root canal treatments and presenting them in an interactive and problem-based paradigm.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of imaging a root canal of a tooth, comprising the steps of:
    generating a first digital radiograph of the tooth from a first orientation;
    transmitting the first digital radiograph to a computer;
    generating a second digital radiograph of the tooth from a second orientation relative to the first orientation;
    transmitting the second digital radiograph to the computer;
    operating the computer to utilize a first projection matrix to generate a first three-dimensional model of surfaces of the root canal of the tooth from the first digital radiograph;
    operating the computer to utilize a second projection matrix to generate a second three-dimensional model of surfaces of the root canal of the tooth from the second digital radiograph;
    operating the computer to determine an intersection of the first three-dimensional model of surfaces of the root canal of the tooth with the second three-dimensional model of surfaces of the root canal of the tooth to define a three-dimensional model of the root canal of the tooth; and
    imaging the three dimensional model of the root canal of the tooth on a display in communication with the computer.

2. The method of imaging of claim 1, wherein the second orientation is angularly spaced from at least 5° relative to the first orientation.

3. The method of claim 1, further comprising the step of calculating a length and curvature of the root canal of the tooth from the three-dimensional model of the root canal of the tooth.

4. A method of imaging a root canal of a tooth, comprising the steps of:
acquiring a first digital radiograph of the tooth;
transmitting the first digital radiograph to a computer;
acquiring a second digital radiograph of the tooth at an angle relative to the first digital radiograph;
transmitting the second digital radiograph to a computer;
operating the computer to compute elements of a first projection matrix to determine a first three-dimensional model of surfaces of the tooth from the first digital radiograph;
operating the computer to compute elements of a second projection matrix to determine a second three-dimensional model of surfaces of the tooth;
detecting first edges representing the root canal of the tooth from the first three-dimensional model of surfaces of the tooth;
modeling the first edges representing the root canal of the tooth by a first $n^{th}$ order polynomial to define a first surface structure of the root canal of the tooth;
detecting second edges representing the root canal of the tooth from the second three-dimensional model of surfaces of the tooth;
modeling the second edges representing the root canal of the tooth by a second $n^{th}$ order polynomial to define a second surface structure of the root canal of the tooth;
operating the computer to determine an intersection of the first surface structure of the root canal of the tooth with the second structure of the root canal of the tooth to define a three-dimensional model of the root canal of the tooth; and
imaging the three-dimensional model of the root canal of the tooth on a display in communication with the computer.

5. The imaging method of claim 4, wherein the second digital radiograph is acquired at an angle of at least 5° relative to the first digital radiograph.

6. The imaging method of claim 4, wherein the first and second edges are detected automatically by the computer after filtering.

7. The imaging method of claim 6, wherein automatic edge detection is accomplished through selection of a single threshold value.

8. The imaging method of claim 4, wherein the first and second edges are detected through selection of a single threshold value by a user.

9. The method of claim 4, further comprising the step of calculating a length and curvature of the root canal of the tooth from the three-dimensional model of the root canal of the tooth.

10. A method of determining the dimensions of a root canal of a tooth, comprising the steps of:
generating a first digital radiograph of the tooth from a first orientation;
transmitting the first digital radiograph to a computer;
generating a second digital radiograph of the tooth at a second orientation, the second orientation angularly spaced relative to the first orientation;
operating the computer to determine an angular difference between the first orientation and the second orientation;
operating the computer to utilize a first projection matrix to generate a first three-dimensional model of surfaces of the tooth from the first digital radiograph;
operating the computer to utilize a second projection matrix to generate a second three-dimensional model of surfaces of the tooth from the second digital radiograph;
filtering the first three-dimensional model of the surfaces of the root canal of the tooth;
filtering the second three-dimensional model of the surfaces of the root canal of the tooth;
operating the computer to detect first edges representing the root canal of the tooth from the filtered first three-dimensional model of the surfaces of the tooth;
modeling the first edges representing the root canal of the tooth by a first $n^{th}$ order polynomial to define a first surface structure of the root canal of the tooth;
operating the computer to detect second edges representing the root canal of the tooth from the filtered second three-dimensional model of the surfaces of the tooth;
modeling the second edges representing the root canal of the tooth by a second $n^{th}$ order polynomial to define a second surface structure of the root canal of the tooth;
operating the computer to determine an intersection of the first surface structure of the root canal of the tooth with the second surface structure of the root canal of the tooth to define a three-dimensional model of the root canal of the tooth; and
operating the computer to determine length and surface curvature of the root canal from the three-dimensional model of the root canal of the tooth.

11. The method of determining dimensions of claim 10, wherein the second orientation is angularly spaced at least 5° relative to the first orientation.

12. The method of determining dimensions of claim 10, wherein first and second edges are detected through selection and application of a single threshold value.

13. The method of determining dimensions of claim 12, wherein threshold selection is accomplished by user input.

14. The method of determining dimensions of claim 12, wherein threshold selection is accomplished automatically.

15. An apparatus for imaging a root canal of a tooth, comprising:
a source of radiation;
a processor having memory associated therewith;
a display in communication with said processor;
a sensor in communication with said processor and operable to provide a digital signal representative of a radiograph of the tooth upon exposure to radiation from said source of radiation; and wherein
said processor is operable under control by logic stored in said memory to
i) receive a first digital signal representative of a radiograph of the tooth from said sensor,
ii) receive a second digital signal representative of a radiograph of the tooth from said sensor,
iii) utilize a first projection matrix to generate a first three-dimensional model of surfaces of the root canal of the tooth from the first digital signal,
iv) utilize a second projection matrix to generate a second three-dimensional model of surfaces of the root canal of the tooth from the second digital signal, v) determine an intersection of the first three-dimensional model of surfaces of the root canal of the tooth with the second three-dimensional model of surfaces of the root canal of the tooth to define a three-dimensional model of the root canal of the tooth, and vi) image the three-dimensional model of the root canal of the tooth on said display.

16. The apparatus of claim 15, wherein said processor is further operable under control by logic stored in said memory to calculate a length and curvature of the root canal of the tooth from the three-dimensional model of the root canal of the tooth.

17. The apparatus of claim 15 wherein said processor is further operable under control by logic stored in said memory to calculate an angular difference between the first and second radiographs.

18. The apparatus of claim 15, wherein said processor is further operable under control by logic stored in said memory to:

i) filter the first three-dimensional model of the surfaces of the root canal, ii) filter the second three-dimensional model of the surfaces of the root canal, iii) detect first edges representing the root canal of the tooth from the filtered first three-dimensional model of the surfaces of the root canal, iv) detect second edges representing the root canal of the tooth from the filtered second three-dimensional model of the surfaces of the root canal of the tooth.

19. The apparatus of claim 18, wherein said processor is further under control by logic stored in said memory to:

i) model the first edges by a first $n^{th}$ order polynomial to define a first surface structure of the root canal of the tooth, ii) model the second edges by a second $n^{th}$ order polynomial to define a second surface structure of the root canal of the tooth, and iii) determine an intersection of the first surface structure of the root canal of the tooth with the second surface structure of the root canal of the tooth to define, in part, the three-dimensional model of the root canal of the tooth.

* * * * *